United States Patent [19]
Naito et al.

[11] B 3,985,738
[45] Oct. 12, 1976

[54] 7-(D-α-HYDROXY-2-ARYLACETAMIDO)-3-(TETRAZOLO-[4,5-b]PYRIDAZIN-6-YLTHIOMETHYL)-3-CEPHEM-4-CARBOXYLIC ACIDS

[75] Inventors: Takayuki Naito, Tokyo; Jun Okumura; Hajime Kamachi, both of Yokohama, all of Japan

[73] Assignee: Bristol-Myers Company, New York, N.Y.

[22] Filed: May 24, 1974

[21] Appl. No.: 473,040

[44] Published under the second Trial Voluntary Protest Program on February 10, 1976 as document No. B 473,040.

[52] U.S. Cl. .............................. 260/243 C; 424/246
[51] Int. Cl.² ........................................ C07D 501/20
[58] Field of Search .................................. 260/243 C

[56] References Cited
UNITED STATES PATENTS
3,814,755   6/1974   Naito et al. ...................... 260/243 C
3,855,213   12/1974  Dunn et al. ...................... 260/243 C

*Primary Examiner*—Nicholas S. Rizzo
*Attorney, Agent, or Firm*—Herbert W. Taylor, Jr.

[57] ABSTRACT 7-(D-α-Hydroxy-2-arylacetamido)-3-(tetrazolo-[4,5-b]pyridazin-6-ylthiomethyl)-3-cephem-4-carboxylic acids and their nontoxic, pharmaceutically acceptable salts are valuable as antibacterial agents and are particularly valuable as therapeutic agents in poultry and animals, including man, in the treatment of infectious diseases caused by many Gram-positive and Gram-negative bacteria.

54 Claims, No Drawings

7-(D-α-HYDROXY-2-ARYLACETAMIDO-3-(TETRAZOLO-[4,5-b]PYRIDAZIN-6-YLTHIOMETHYL)3-CEPHEM-4-CARBOXYLIC ACIDS

BACKGROUND OF THE INVENTION

1. Field of the Invention

The cephalosporins of the present invention possess the usual attributes of such compounds and are particularly useful in the treatment of bacterial infections by parenteral administration.

2. Description of the Prior Art

The cephalosporins are a well-known group of semi-synthetic antibacterial agents made originally, for example, by acylation of the 7-amino group of the nucleus 7-aminocephalosporanic acid (7-ACA) and later by similar acylation of nuclei derived therefrom, as by modification of its substituent at the 3-position. Various reviews have appeared in the scientific literature (e.g. Cephalosporins and Penicillins — Chemistry and Biology, edited by Edwin H. Flynn, Academic Press, New York, 1972, and particularly pages 554–569) and in the patent literature, e.g. as in U.S. Pat. Nos. 3,687,948, 3,741,965, 3,759,904, 3,759,905, 3,766,175 and 3,776,906 (all U.S. Class 260–243C).

Issued patents on 3-thiolated cephalosporins in which the 7-substituent is a. α-Amino-α-phenylacetamido include U.S. Pat. No. 3,641,021, U.S. Pat. No. 3,734,907, U.S. Pat. No. 3,687,948, U.S. Pat. No. 3,741,965, U.S. Pat. No. 3,757,015, U.S. Pat. No. 3,743,644, Japan Pat. No. 71/24400 (Farmdoc 46374S), Belgium Pat. No. 776,222 (Farmdoc 38983T; U.K. Pat. No. 1,328,340 which includes various substituents on the benzene ring), Belgium Pat. No. 772,592 (Farmdoc 19696T; U.S. Pat. Nos. 3,687,948, 3,734,907 and 3,757,012), West Germany Pat. No. 2,202,274 (Farmdoc 50428T) corresponding to U.S. Pat. No. 3,759,904, Netherlands Pat. No. 7205644 (farmdoc 76309T; U.S. Pat. No. 3,757,014); and b. o-, m- or p-aminoethoxyphenylacetamido as Netherlands 72/13968 (Farmdoc 24740U) corresponding to U.S. Pat. No. 3,759,905 and c. o-aminomethylphenylacetamido as Netherlands Pat. No. 72/06326 (Farmdoc 76374T) (which also reviews the older patent literature concerning substituted 7-phenylacetamidocephalosporanic acids) corresponding to U.S. Pat. Nos. 3,766,176 and 3,766,175; and d. N-(phenylacetimidoyl)aminoacetamido as U.S. Pat. No. 3,692,779; and e. α-amino-α-(1,4-cyclohexadienyl)acetamido as in Belgium Pat. No. 776,222 (Farmdoc 38983T; U.K. Pat. No. 1,328,340).

Additional similar disclosures are found in U.S. Pat. No. 3,692,779 (Belgium Pat. No. 771,189; Farmdoc 12819T), Japan Pat. No. 72/05550 (Farmdoc 12921T), Japan Pat. No. 72/05551 (Farmdoc 12922T), U.S. Pat. No. 3,719,673 (Belgium Pat. No. 759,570; Farmdoc 39819S), Belgium Pat. No. 793,311 (Farmdoc 39702U) and Belgium Pat. No. 793,191 (Farmdoc 39684U).

Issued disclosures of 3-thiolated cephalosporins in which the 7-substituent is 7-mandelamido (7-α-hydroxyphenylacetamido) are found, for example, in U.S. Pat. No. 3,641,021, France Pat. No. 73.10112, U.S. Pat. No. 3,796,801, Great Britain Pat. No. 1,328,340 (Farmdoc 38983T), U.S Pat. No. 3,701,775, Japan Pat. No. 4844293 (Farmdoc 55334U) and in Hoover et al., J. Med. Chem. 17(1), 34–41 (1974) and Wick et al., Antimicrobial Ag. Chemo., 1(3), 221–234 (1972).

SUMMARY OF THE INVENTION

This invention comprises the acids having the D configuration in the 7-sidechain and the formula

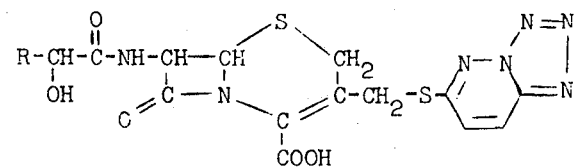

wherein R is

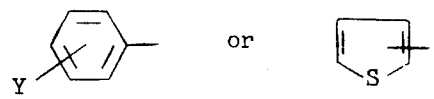

and Y is hydrogen, chlorine, bromine, fluorine, trifluoromethyl, amino, nitro, hydroxy, loweralkyl of 1–4 carbon atoms or lower alkoxy of 1–4 carbon atoms and the nontoxic, pharmaceutically acceptable salts of those acids and the easily hydrolyzed esters of those acids including especially the pivaloyloxymethyl, acetoxymethyl, acetonyl, phenacyl and methoxymethyl esters and the silyl esters such as the trimethylsilyl ester.

In the preferred embodiments of this invention R is 2-thienyl, 3-thienyl, phenyl, chlorophenyl, bromophenyl, trifluoromethylphenyl, tolyl or methoxyphenyl.

Such salts include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)-alkylpiperidine, e.g. N-ethylpiperidine, and other amines which have been used to form salts with benzylpenicillin.

A particularly preferred embodiment of this invention comprises the acid having the D configuration in the 7-sidechain and the formula

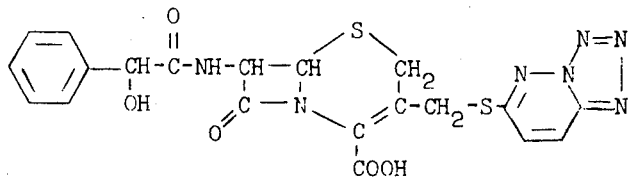

and its nontoxic, pharmaceutically acceptable salts and easily hydrolyzed esters.

Also included in this invention are the compounds (used as either intermediates or metabolic precursors) in which the α-hydroxy group is "blocked" by substituents such as dichloroacetyl (U.K. Pat. No. 962,024 and U.K. Pat. No. 1,328,340), formyl (U.S. Pat. No. 3,641,021), trimethylsilyl or tetrahydropyranyl (U.K. Pat. No. 1,328,340).

There is also provided, according to the present invention, the process for the preparation of the compound having the formula

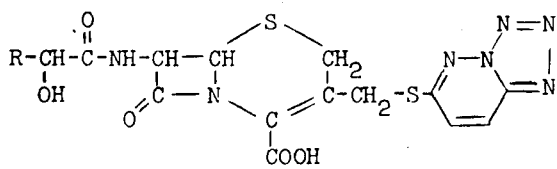

wherein R is as defined above and the nontoxic salts and easily hydrolyzed esters thereof which comprises reacting the compound of the formula

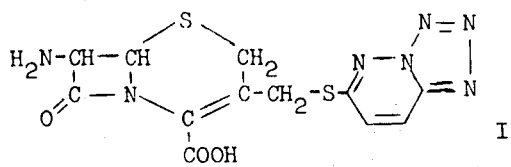 II or a salt or easily hydrolyzed ester or Schiff base (as with benzaldehyde) thereof with an acylating derivative of the acid (in which the hydroxy group may be protected) having the formula

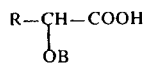

wherein R is as defined above and wherein B represents hydrogen or the protecting group (that is, with that acid or its reactive derivative substituted at the carboxyl group) to produce the compound (in which the hydroxyl group may be protected) having the formula

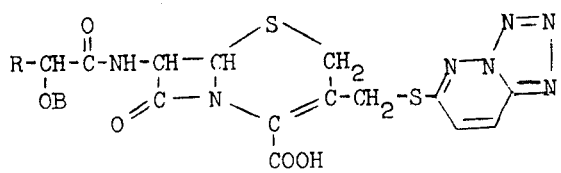

or the corresponding salt or easily hydrolyzed ester thereof wherein B represents hydrogen or the protecting group, and if such a protecting group is present subsequently subjecting the resulting compound to chemical removal of the protecting group, that is, subjecting the resulting compound to elimination reaction of the protecting group.

The compound of the present invention is prepared according to the present invention by coupling with a particular 3-thiolated-7-aminocephalosporanic acid designated II, that is, 7-amino-3-(tetrazolo[4,5-b]pyridazin-6-ylthiomethyl)-3-cephem-4-carboxylic acid or a salt or easily hydrolyzed ester or Schiff base as with benzaldehyde thereof (including, but not limited to, those of U.S. Pat. No. 3,284,451 and U.K. Pat. No. 1,229,453 and any of the silyl esters described in U.S. Pat. No. 3,249,622 for use with 7-aminopenicillanic acid and used in Great Britain Pat. No. 1,073,530 and particularly the pivaloyloxymethyl, acetoxymethyl, methoxymethyl, acetonyl, phenacyl, p-nitrobenzyl and β, β, β, -trichloroethyl esters) D-mandelic acid or a substituted D-mandelic acid as described herein or their functional equivalent as an acylating agent for a primary amino group. After coupling, any hydroxy blocking group present is removed to give the desired product.

Thus, with respect to said substituted or unsubstituted D-mandelic acid to be used to couple with compound II, functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. A particularly useful anhydride is D-mandelic acid carboxyanhydride (U.S. Pat. No. 3,167,549) or the corresponding substituted D-mandelic acid carboxyanhydride. In addition, an acid azide or an active ester or thioester (e.g., with p-nitrophenyl, 2,4-dinitrophenyl, thiophenol, thioacetic acid) may be used or the free acid itself may be coupled with compound II after first reacting said free acid with N,N'-dimethylchloroformiminium chloride [cf. Great Britain 1,008,170 and Novak and Weichet, Experientia XXI, 6, 360 (1965)] or by the use of enzymes or of an N,N'-carbonyldiimidazole or an N,N'-carbonylditriazole [cf. South African patent specification 63/2684] or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkylylamine reagent [cf. R. Buijle and H. G. Viehe, Angew. Chem. International Edition 3, 582, (1964)] or of an isoxasolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958)] or of hexachlorocyclotriphosphatiazine or hexabromocyclotriphosphatriazine (U.S. Pat. No. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595-1598 (1973)] or of diphenyl phosphite [Tetrahedron Letters No. 49, pp. 5047–5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. Pat. No. 3,682,777.

For the coupling of the substituted or unsubstituted D-mandelic acid (with or without a protecting group on the α-hydroxyl) as described above with compound II (or a salt or preferably an easily hydrolyzed ester or Schiff base, as with benzaldehyde, thereof) it is also convenient and efficient to utilize as the coupling agent N-ethoxycarbonyl-2-ethoxy-1,2-dihydroquinoline (EEDQ) as described in J. Amer. Chem. Soc., 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a substituted or unsubstituted D-mandelamido-cephalosporanic acid (in which the α-hydroxy group is protected or unprotected and so is the carboxyl group) with 6-mercaptotetrazolo[4,5-b] pyridazine and then removing the protecting group if any is present on the α-hydroxy group or on the carboxyl group or both. The displacement of such an acetoxy group with such a thiol is a well-known reaction and may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. Such substituted or unsubstituted D-mandelamido-cephalosporanic acids are prepared by the procedures described generally or specifically in J. Med. Chem. 17(1), 34-41 (1974) and the references cited therein.

In the treatment of bacterial infections in man, the compounds of this invention are administered parenterally, in accordance with conventional procedures for antibiotic administration, in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitably physiologically acceptable carriers or excipients. The dosage units are preferably in the form of liquid preparations such as solutions or suspensions.

STARTING MATERIALS

Preparation of 6-Mercaptotetrazolo[4,5-b]pyridazine

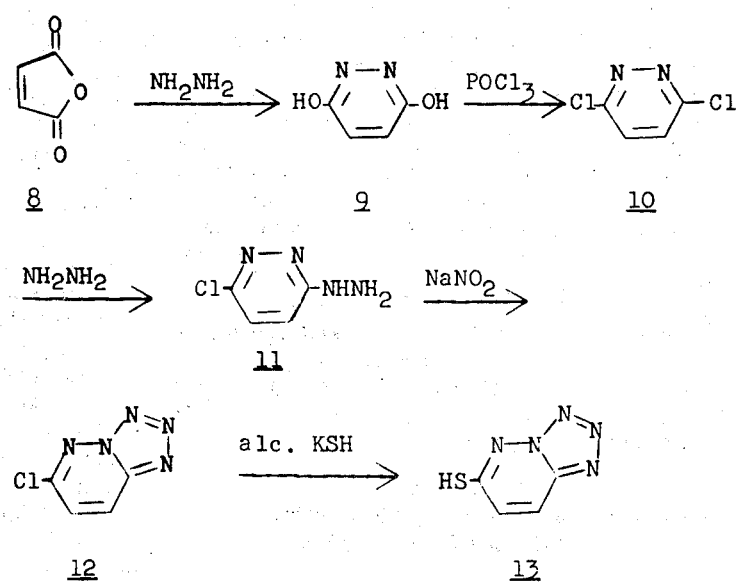

3,6-Dihydroxypyridazine (9)

To a boiling solution of 315 g. (3 moles) of hydrazine dihydrochloride in 2 L of water was added portionwise 295 g. (3 moles) of finely ground maleic anhydride 8 with stirring. After the addition was completed the heating was continued for 4 hours and then allowed to stand overnight in a refrigerator to give 285 g. (85%) of 9 as massive pillars. m.p. >290° C.

3,6-Dichloropyridazine (10)

A mixture of 150 g. (1.33 moles) of 9 and 250 g. of phosphorus oxychloride was refluxed for 3 hours under protection from moisture. The excess of phosphorus oxychloride was removed under reduced pressure and the dark residue was poured into one Kg. of crushed ice. The resulting precipitate was collected by filtration. The second crop of the product was obtained from the mother liquor by the extraction with five 300 ml. portions of chloroform followed by treating with 1 g. of charcoal and evaporating the solvent. The first and second crop were combined, dissolved in 500 ml. of chloroform and treated again with one g. of charcoal and concentrated to give 165 g. (83%) of 10 as fine needles melting at 60°–61° C. (in a sealed tube).

3-Chloro-6-hydrazinopyridazine (11)

A mixture of 40 g. (0.27 mole) of 3,6-dichloropyridazine (10) and 40 ml. of 80% hydrazine hydrate in 80 ml. of ethanol was refluxed for one hour. The reaction mixture was evaporated to dryness and the residue was recrystallized from benzene to give 39 g. (100%) of 11 melting at 114°–115° C.

6-Chlorotetrazolo[4,5-b]pyridazine (12)

To a solution of 25.7 g. (0.174 mole) of 11 in 100 ml. of 15% acetic acid was added dropwise a solution of 13.8 g. (0.2 mole) of sodium nitrite in 50 ml. of water with vigorous stirring at 5°–10° C. Stirring was continued for one hour at the same temperature. The precipitate which separated was filtered, washed with 20 ml. of water and air-dried to give 17.02 g. of 12. Additional product was obtained by evaporation of the filtrate. Total yield 18.32 g. (64%). M.p. 104°–105° C.

6-Mercaptotetrazolo[4,5-b]pyridazine (13)

A mixture of 21.3 g. (0.137 mole) of 12 and 20 g. (0.25 mole) of potassium hydrosulfide in 200 ml. of ethanol was refluxed for 2 hours and evaporated to dryness. The residue was dissolved in 100 ml. of water and filtered to remove a small amount of insoluble material. The filtrate was acidified to pH 1 with dil. hydrochloric acid to precipitate (13) as colorless needles which were collected by filtration, washed with 20 ml. of water and dried. Yield 9.80 g. (47%). M.p. 140°–141° C. (dec.).

IR: $\gamma_{max}^{KBr}$ 2500, 1540, 1445, 1295, 840 cm$^{-1}$.

NMR: $\sigma_{ppm}^{D_2O+K_2CO_3}$ 7.44 (1 H, d, 10 Hz, pyridazine-H), 7.77 (1 H, d, 10 Hz, pyridazine-H).

Anal. Calcd. for C$_4$H$_3$N$_5$S: C, 31.37; H, 1.97; N, 45.72; S, 20.94. Found: C, 31.52; 31.66; H, 1.70; 1.69; N, 46.01; 46.01; S, 20.95.

Preparation of 7-amino-3-(tetrazolo[4,5-b]pyridazin-6-ylthiomentyl)-3-cephem-4-carboxylic acid (3)

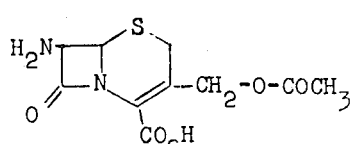

7-ACA

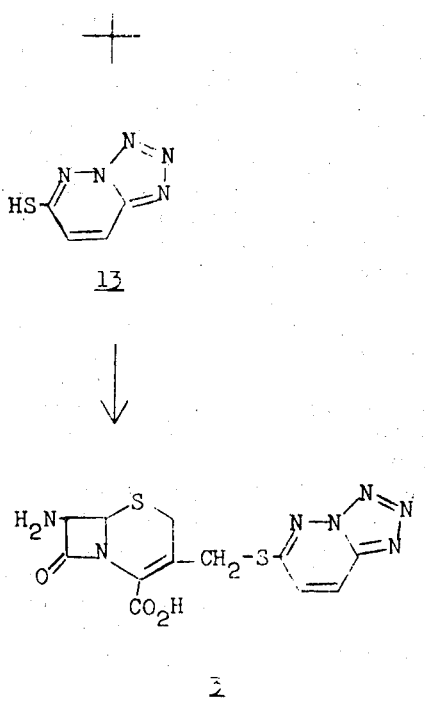

7-Amino-3-(tetrazolo[4,5-b]pyridazin-6-ylthiomehtyl)-3-cephem-4-carboxylic acid (3).

i. To a hot solution (50°–60° C.) of 9.56 g. (0.062 mole) of 13 and 10.42 g. (0.124 mole) of sodium bicarbonate in 300 ml. of water was added carefully 16.86 g. (0.062 mole) of 7-ACA and the mixture was heated at 80°–85° C. for 30 minutes. About 7 g. of sodium bicarbonate was added to the reaction mixture to dissolve insoluble material. The solution was treated with active carbon, filtered and the filtrate was acidified to pH 5 with dil. hydrochloric acid. The precipitate was collected by filtration, washed with water, air-dried and finally in vacuo on P$_2$O$_5$ to give 14.47 g. (64%) of 7-amino-3-(tetrazole[4,5-b]-pyridazin-6-ylthiomehtyl)-3-cephem-4-carboxylic acid 3. M.p. 248°–250° C. (dec.).

ii. A stirred solution of 16.8 g. (0.11 mole) of 13 and 18.48 g. (0.22 mole) of NaHCO$_3$ in 1 L of 0.1 M phosphate butter (pH 6.4) was heated at 50° C. and to the solution was added portionwise 30 g. (0.11 mole) of 7-ACA. The mixture was heated at 80° C. for 2.5 hours, during which period insoluble material still remained. The reaction mixture was cooled to room temperature and the precipitated 7-amino-3-(tetrazolo[4,5-b]pyridazin-6-ylthiomethyl)-3-cephem-4-carboxylic acid (3) was collected by filtration, washed thoroughly with 200 ml. of water and air-dried.

Additional 3 was obtained from the filtrate and the washings by acidifying to pH 5 with dil. HCl.

Total yield 32.9 g. (83%). M.p. 245°–250° C. (dec.).

IR: $\nu_{max}^{KBr}$ 1800, 1615, 1538, 1360 cm$^{-1}$.

UV: $\lambda_{max}^{1\%}$ NaHCO$_3$ 237 nm ($\epsilon$19500), 275 nm ($\epsilon$12000), 310 nm (sh) ($\epsilon$5700).

NMR: $\delta_{ppm}^{D_2O+K_2CO_3}$ 3.35 (1H, d, 18 Hz, 2-H), 3.76 (1 H, d, 18 Hz, 2-H), 4.00 (1 H, d, 10 Hz, 3-CH$_2$), 4.48 (1 H, d, 10 Hz, 3-CH$_2$), 4.93 (1 H, d, 4 Hz, 6-H), 5.32 (1 H, d, 4 Hz, 7-H), 7.46 (1 H, d, 10 Hz, pyridazine-H), 8.18 (1 H, d, 10 Hz, pyridazine-H).

Anal. Calcd. for $C_{12}H_{11}N_7O_3S_2C$, C. 39.44; H, 3.03; N, 26.83; S, 17.55. Found: C, 39.19; H, 2.71; N, 26.84; S, 17.35.

Pivaloyloxymethyl 7-Amino-3-(tetrazolo[4,5-b]pyridazin-6-ylthiomethyl)-3-cephem-4-carboxylate.

Method A. — The title compound is produced by substituting for the 7-aminocephalosporanic acid used immediately above an equimolar weight of pivaloyloxymethyl 7-aminocephalosporanate hydrochloride prepared according to Example 2 of U.K. Pat. No. 1,229,453 from 7-aminocephalosporanic acid. German Pat. No. 1,904,585 (Farmdoc 39,445) is equivalent to U.K. Pat. No. 1,229,453.

Method B. — The title compound is produced by substituting for the 0.025 mole (6.8 g.) 7aminocephalosporanic acid used in the procedure of Example 2 of U.K. Pat. No. 1,229,453 an equimolar weight of 7-amino-3-(tetrazolo[4,5-b]pyridazin-6-ylthiomethyl)-3-cephem-4-carboxylic acid.

The respective acetoxymethyl, methoxymethyl, acetonyl and phenacyl esters of 7-amino-3-(tetrazolo[4,5-b]-pyridazin-6-ylthiomethyl)-3-cephem-4-carboxylic acid are prepared by substituting in Method B above for the chloromethyl pivalate used therein an equimolar weight of chloromethyl acetate, chloromethyl methyl ether, chloroacetone and phenacyl bromide, respectively.

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group and the first three are also of interest beacuse on oral administration they provide different rates and amounts of absorption and give differing concentrations of the active antibacterial agent in blood and tissues.

These five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767–773 (1971). In another good method the triethylamine salt of 7-aminocephalosporanic acid is reacted directly with the active halogen compound, as in U.K. Pat. No. 1,229,453.

These esters of 7-aminocephalosporanic acid are then reacted with the nucleophile 6-mercaptotetrazolo[4,5-b]pyridazine in the same manner as is illustrated herein for 7-aminocephalosporanic acid itself. The 3-thiolated ester of 7-aminocephalosporanic acid is then coupled with the substituted or unsubstituted D-mandelic acid. Before or after removal of any blocking group on the α-hydroxy group of the 7-sidechain, the ester of the cephalosporin so obtained is, if not used per se, converted to its free acid, including if desired, any salt by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006–2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

Preparation of D-mandelic acid carboxyanhydride

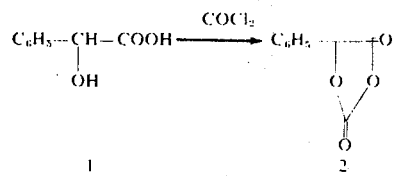

D-Mandelic acid carboxyanhydride (2)

Phosgene was bubbled through a solution of 2.0 g. (0.013 mole) of D(-)-mandelic acid (1) in dry tetrahydrofuran for 30 minutes. The solution was allowed to stand overnight after which time it was heated under reflux for 10 minutes. Evaporation of the solvent under reduced pressure afforded an oily residue which was solidified by trituration with n-hexane (20 ml.). The product was collected by filtration and dried in vacuo on KOH. Yield 2.3 g. of D-mandelic acid carboxyanhydride.

IR: $\nu_{max}^{nuj}$ 1895, 1875, 1780 cm$^{-1}$.

The preferred and most active compounds of the present invention are those having the D configuration at the α-carbon atom in the 7-side-chain, that is, those made from D-mandelic acid or a monosubstituted D-mandelic acid as illustrated herein. In addition, the configuration at the two optically active, asymmetric centers in the β-lactam nucleus is that found in cephalosporin C produced by fermentation and in the 7-aminocephalosporanic acid derived therefrom.

The following examples are given in illustration of, but not in limitation of, the present invention. All temperatures are in degrees Centigrade. 7-Aminocephalosporanic acid is abbreviated as 7-ACA; -ACA- represents the moiety having the structure

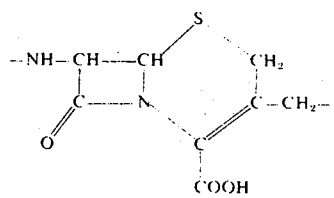

and thus 7-ACA can be represented as

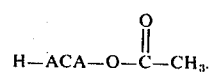

Methyl isobutyl ketone is represented as MIBK. "Skellysolve B" is a petroleum ether fraction of B.P. 60–68° C. consisting essentially of n-hexane.

DESCRIPTION OF THE PREFERRED EMBODIMENTS

EXAMPLE 1

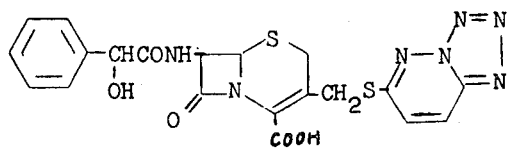

4, BB-S266

BB-S266;
7-(D-α-Hydroxy-α-phenylacetamido)-3-(tetrazolo[4,5-b]pyridazin-6-ylthiomethyl)-3-cephem-4-carboxylate (4)

D-(−)-Mandelic acid carboxyanhydride (2) (0.53 g., 3 mmoles) was added portionwise to a stirred solution of 7-amino-3-(tetrazolo[4,5-b]pyridazin-6-ylthiomethyl)-3-cephem-4-carboxylic acid (3) (0.73 g., 2 mmoles) and NaHCO$_3$ (0.84 g., 10 mmoles) in 20 ml. of 50% aqueous acetone at 0° C. The reaction mixture was stirred at room temperature for one hour and washed with ether (30 ml.). The aqueous layer was acidified to pH 2 with dil. HCl and extracted with ethyl acetate (2 × 50 ml) treated with a small amount of active carbon and dried on anhydrous sodium sulfate. Removal of the solvent under reduced pressure afforded an oily residue which was triturated with ether (50 ml.) to give 7-(D-α-hydroxy-α-phenylacetamido)-3-(tetrazolo[4,5-b]pyridazin-6-ylthiomethyl)-3-cephem-4-carboxylic acid (4). Yield 0.24 g. (24%). M.p. 130°–135° C. (dec.).

IR: $\nu_{max}^{KBr}$ 1770, 1720, 1675, 1520 cm$^{-1}$.
UV: $\lambda_{max}^{EtOH}$ 243 nm ($\epsilon$, 17000), 274 nm(sh) ($\epsilon$, 9500), 314 nm ($\epsilon$, 4500).
NMR: $\delta_{ppm}^{DMSO-d}$ 4.12 (1H, d, 12 Hz, 3-C$\underline{H}_2$), 4.70 (1H, d, 12 Hz, 3-C$\underline{H}_2$), 5.00-6.00 (3H, m, 6-H, 7-H and C$\underline{H}$OH), 7.2 - 7.7 (5H, m, phenyl-H), 7.94 (1H, d, 10 Hz, pyridazine-H), 8.70 (1H, d, 10 Hz, pyridazine-H).

In vitro Antibacterial Activity of BB-S266 by Tube Dilution Method (Nutrient Broth).

| Organisms | MIC (mcg./ml.) BB-S266 |
|---|---|
| S. aureus Smith | 0.1 |
| S. aureus Smith + 50% serum | 0.2 |
| S. aureus BX-1633 | 0.8 |
| S. aureus Russel | 0.4 |
| St. pyogenes A9604 | 0.01 |
| Dip. pneumoniae | 0.01 |
| Mycobacterium 607 | >100 |
| E. coli NIHJ | 0.08 |
| E. coli ATCC 8739 | 1.6 |
| E. coli Juhl A15119 | 3.1 |
| Kl. pneumoniae A9977 | 3.1 |
| Kl. pneumoniae A15130 | 3.1 |
| Pr. mirabilis A9900 | 6.3 |
| Pr. morganii A15153 | 50 |
| Sal. enteritidis A9531 | 0.4 |
| Ser. marcescens A20019 | 100 |
| Ps. aeruginosa A9843 | >100 |

EXAMPLE 2

Sodium 6-[D-α-hydroxy-α-phenylacetamido]-3-(tetrazolo[4,5-b]pyridazin-6-ylthiomethyl)-3-cephem-4-carboxylate To a solution of 4 (2.1 mmoles) in 20 ml. of THF is added 2.2 ml. of sodium 2-ethylhexanoate (1M, ethyl acetate solution) under stirring at room temperature. The solution is diluted with ethyl acetate (100 ml.) to afford a precipitate, which is washed well with ethyl acetate to give solid sodium 6-(D-α-hydroxy-α-phenylacetamido)-3-(tetrazolo[4,5-b]pyridazin-6-ylthiomethyl)-3-cephem-4-carboxylate.

EXAMPLE 3

Substitution for the D-mandelic acid carboxyanhydride in the procedure of Example 1 of an equimolar weight of the carboxyanhydrides prepared in similar fashion from the monosubstituted D-mandelic acids
D-2-chloro-mandelic acid,
D-3-chloro-mandelic acid,
D-4-chloro-mandelic acid,
D-2-bromo-mandelic acid,
D-3-bromo-mandelic acid,
D-4-bromo-mandelic acid,
D-2-fluoro-mandelic acid,
D-3-fluoro-mandelic acid,
D-4-fluoro-mandelic acid,
D-2-trifluoromethyl-mandelic acid,
D-3-trifluoromethyl-mandelic acid,
D-4-trifluoromethyl-mandelic acid,
D-2-amino-mandelic acid,
D-3-amino-mandelic acid,
D-4-amino-mandelic acid,
D-2-nitro-mandelic acid,
D-3-nitro-mandelic acid,
D-4-nitro-mandelic acid,
D-2-hydroxy-mandelic acid,
D-3-hydroxy-mandelic acid,
D-4-hydroxy-mandelic acid,
D-2-methyl-mandelic acid,
D-3-methyl-mandelic acid,
D-4-methyl-mandelic acid,
D-2-methoxy-mandelic acid,
D-3-methoxy-mandelic acid and
D-4-methoxy-mandelic acid respectively produces 7-(D-2-chloro-mandelamido)-3-(tetrazolo[4,5-b]pyridazin-6-ylthiomethyl)-3-cephem-4-carboxylic acid,
7-(D-3-chloro-mandelamido)-3-(tetrazolo[4,5-b]pyridazin-6-ylthiomethyl)-3-cephem-4-carboxylic acid,
7-(D-4-chloro-mandelamido)-3-(tetrazolo[4,5-b]pyridazin-6-ylthiomethyl)-3-cephem-4-carboxylic acid,
7-(D-2-bromo-mandelamido)-3-(tetrazolo[4,5-b]pyridazin-6-ylthiomethyl)-3-cephem-4-carboxylic acid,
7-(D-3-bromo-mandelamido)-3-(tetrazolo[4,5-b]pyridazin-6-ylthiomethyl)-3-cephem-4-carboxylic acid,
7-(D-4-bromo-mandelamido)-3-(tetrazolo[4,5-b]pyridazin-6-ylthiomethyl)-3-cephem-4-carboxylic acid, 7-(D-2-fluoro-mandelamido)-3-(tetrazolo[4,5-b]pyridazin-6-ylthiomethyl)-3-cephem-4-carboxylic acid,
7-(D-3-fluoro-mandelamido)-3-(tetrazolo[4,5-b]pyridazin-6-ylthiomethyl)-3-cephem-4-carboxylic acid,
7-(D-4-fluoro-mandelamido)-3-(tetrazolo[4,5-b]pyridazin-6-ylthiomethyl)-3-cephem-4-carboxylic acid,
7-(D-2-trifluoromethyl-mandelamido)-3-(tetrazolo[4,5-b]pyridazin-6-ylthiomethyl)-3-cephem-4-carboxylic acid,
7-(D-3-trifluoromethyl-mandelamido)-3-(tetrazolo[4,5-b]pyridazin-6-ylthiomethyl)-3-cephem-4-carboxylic acid,
7-(D-4-trifluoromethyl-mandelamido)-3-(tetrazolo[4,5-b]pyridazin-6-ylthiomethyl)-3-cephem-4-carboxylic acid,
7-(D-2-amino-mandelamido)-3-(tetrazolo[4,5-b]pyridazin-6-ylthiomethyl)-3-cephem-4-carboxylic acid,
7-(D-3-amino-mandelamido)-3-(tetrazolo[4,5-b]pyridazin-6-ylthiomethyl)-3-cephem-4-carboxylic acid,
7-(D-4-amino-mandelamido)-3-(tetrazolo[4,5-b]pyridazin-6-ylthiomethyl)-3-cephem-4-carboxylic acid,
7-(D-2-nitro-mandelamido)-3-(tetrazolo[4,5-b]pyridazin-6-ylthiomethyl)-3-cephem-4-carboxylic acid,
7-(D-3-nitro-mandelamido)-3-(tetrazolo[4,5-b]pyridazin-6-ylthiomethyl)-3-cephem-4-carboxylic acid,
7-(D-4-nitro-mandelamido)-3-(tetrazolo[4,5-b]pyridazin-6-ylthiomethyl)-3-cephem-4-carboxylic acid,
7-(D-2-hydroxy-mandelamido)-3-(tetrazolo[4,5-b]pyridazin-6-ylthiomethyl)-3-cephem-4-carboxylic acid,
7-(D-3-hydroxy-mandelamido)-3-(tetrazolo[4,5-b]pyridazin-6-ylthiomethyl)-3-cephem-4-carboxylic acid,
7-(D-4-hydroxy-mandelamido)-3-(tetrazolo[4,5-b]pyridazin-6-ylthiomethyl)-3-cephem-4-carboxylic acid,
7-(D-2-methyl-mandelamido)-3-(tetrazolo[4,5-b]pyridazin-6-ylthiomethyl)-3-cephem-4-carboxylic acid,
7-(D-3-methyl-mandelamido)-3-(tetrazolo[4,5-b]pyridazin-6-ylthiomethyl)-3-cephem-4-carboxylic acid,
7-(D-4-methyl-mandelamido)-3-(tetrazolo[4,5-b]pyridazin-6-ylthiomethyl)-3-cephem-4-carboxylic acid,
7-(D-2-methoxy-mandelamido)-3-(tetrazolo[4,5-b]pyridazin-6-ylthiomethyl)-3-cephem-4-carboxylic acid,
7-(D-3-methoxy-mandelamido)-3-(tetrazolo[4,5-b]pyridazin-6-ylthiomethyl)-3-cephem-4-carboxylic acid and
7-(D-4-methoxy-mandelamido)-3-(tetrazolo[4,5-b]pyridazin-6-ylthiomethyl)-3-cephem-4-carboxylic acid respectively.

EXAMPLE 4

Substitution for the D-mandelic acid carboxyanhydride in the procedure of Example 1 of an equimolar weight of the carboxyanhydride prepared in similar fashion from D-2-thiopheneglycolic acid and D-3-thiopheneglycolic acid respectively produces 7-(D-α-hydroxy-2-thienylacetamido)-3-(tetrazolo[4,5-b]-pyridazin-6-ylthiomethyl)-3-cephem-4-carboxylic acid and 7-(D-α-hydroxy-3-thienylacetamido)-3-(tetrazolo[4,5-b]-pyridazin-6-ylthiomethyl)-3-cephem-4-carboxylic acid respectively.

EXAMPLE 5

7-(D-α-Hydroxy-α-phenylacetamido)-3-(tetrazolo[4,5-b]pyridazin-6-ylthiomethyl)-3-cephem-4-carboxylic acid prepared from 7-D-mandelamidocephalosporanic acid.

0.27 Mole of sodium 7-D-mandelamidocephalosporanate is suspended in 1000 ml. of 0.1 M phosphate buffer of pH 6.4 and there is added 0.31 moles of 6-mercaptotetrazolo[4,5-b]pyridazine. The solution is heated at 55° C. under a nitrogen atmosphere for five hours. After one hour the pH is adjusted to 6.4 by addition of a small amount of 40% $H_3PO_4$. At the end of the five hour heating period the solution is cooled to 23° C. and the pH adjusted to 2 by the addition of 3 N HCl under a layer of ethyl acetate. The product is extracted into ethyl acetate and stirred for 15 min. at 23° C. with 2 g. of ("Darco KB") decolorizing charcoal. The mixture is then filtered through a pad of diatomaceous earth ("Celite") and the ethyl acetate removed from the filtrate under vacuum. The residue is triturated to a solid with diethyl ether, collected by filtration and dried over $P_2O_5$ under vacuum to yield solid 7-(D-α-hydroxy-α-phenylacetamido)-3-(tetrazolo[4,5-b]pyridazin-6-ylthiomethyl)-3-cephem-4-carboxylic acid.

We claim:
1. An acid having the D configuration in the 7-sidechain and the formula

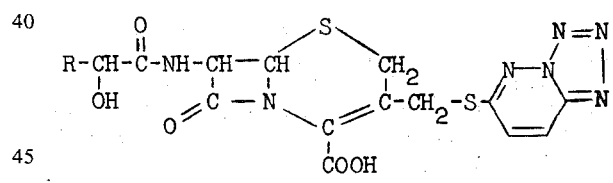

wherein R is

and Y is hydrogen, chlorine, bromine, fluorine, trifluoromethyl, amino, nitro, hydroxy, lower alkyl of 1–4 carbon atoms or lower alkoxy of 1–4 carbon atoms.
2. The sodium salt of an acid of claim 1.
3. The potassium salt of an acid of claim 1.
4. A nontoxic, pharmaceutically acceptable salt of an acid of claim 1.
5. A pivaloyloxymethyl ester of an acid of claim 1.
6. An acetoxymethyl ester of an acid of claim 1.
7. An acetonyl ester of an acid of claim 1.
8. A phenacyl ester of an acid of claim 1.

9. A methoxymethyl ester of an acid of claim 1.
10. An acid of claim 1 having the D configuration in the 7-sidechain and the formula

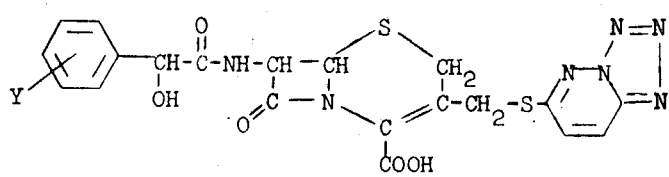

wherein Y is hydrogen, chlorine, bromine, fluorine, trifluoromethyl, amino, nitro, hydroxy, lower alkyl of 1–4 carbon atoms or lower alkoxy of 1–4 carbon atoms.

11. The sodium salt of an acid of claim 10.
12. The potassium salt of an acid of claim 10.
13. A nontoxic, pharmaceutically acceptable salt of an acid of claim 10.
14. A pivaloyloxymethyl ester of an acid of claim 10.
15. An acetoxymethyl ester of an acid of claim 10.
16. An acetonyl ester of an acid of claim 10.
17. A phenacyl ester of an acid of claim 10.
18. A methoxymethyl ester of an acid of claim 10.
19. The acid of claim 1 having the D configuration in the 7-sidechain and the formula

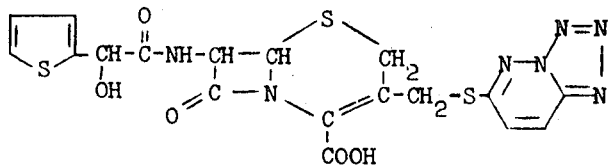

20. The sodium salt of the acid of claim 19.
21. The potassium salt of the acid of claim 19.
22. A nontoxic, pharmaceutically acceptable salt of the acid of claim 19.
23. The pivaloyloxymethyl ester of an acid of claim 19.
24. The acetoxymethyl ester of an acid of claim 19.
25. The acetonyl ester of an acid of claim 19.
26. The phenacyl ester of an acid of claim 19.
27. The methoxymethyl ester of an acid of claim 19.
28. The acid having the D configuration in the 7-sidechain and the formula

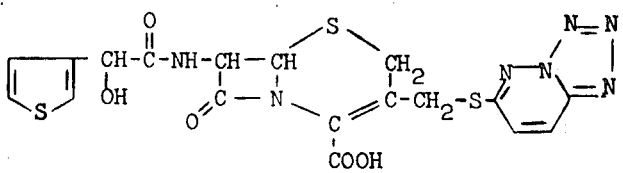

29. The sodium salt of the acid of claim 28.
30. The potassium salt of the acid of claim 28.
31. A nontoxic, pharmaceutically acceptable salt of the acid of claim 28.
32. The pivaloyloxymethyl ester of an acid of claim 28.
33. The acetoxymethyl ester of an acid of claim 28.
34. The acetonyl ester of an acid of claim 28.
35. The phenacyl ester of an acid of claim 28.
36. The methoxymethyl ester of an acid of claim 28.
37. An acid of claim 1 having the D configuration in the 7-sidechain and the formula

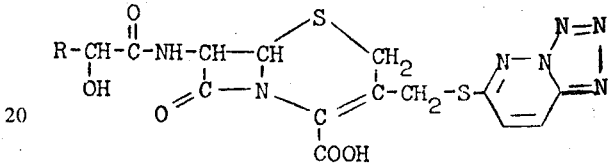

wherein R is chlorophenyl, bromophenyl, trifluoromethylphenyl, tolyl or methoxyphenyl.

38. The sodium salt of an acid of claim 37.
39. The potassium salt of an acid of claim 37.
40. A nontoxic, pharmaceutically acceptable salt of an acid of claim 37.
41. A pivaloyloxymethyl ester of an acid of claim 37.
42. An acetoxymethyl ester of an acid of claim 37.
43. An acetonyl ester of an acid of claim 37.
44. A phenacyl ester of an acid of claim 37.
45. A methoxymethyl ester of an acid of claim 37.
46. The acid having the D configuration in the 7-sidechain and the formula

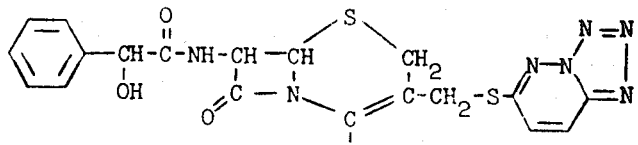

47. The sodium salt of the acid of claim 46.
48. The potassium salt of the acid of claim 46.
49. A nontoxic, pharmaceutically acceptable salt of the acid of claim 46.
50. The pivaloyloxymethyl ester of an acid of claim 46.
51. The acetoxymethyl ester of an acid of claim 46.
52. The acetonyl ester of an acid of claim 46.
53. The phenacyl ester of an acid of claim 46.
54. The methoxymethyl ester of an acid of claim 46.

* * * * *